United States Patent
Salemi et al.

(10) Patent No.: US 8,348,889 B2
(45) Date of Patent: Jan. 8, 2013

(54) SELF-RETAINING AND FLUID DELIVERY CATHETER

(76) Inventors: Arash Salemi, New York, NY (US); Curtis Anderson, Greenville, NC (US)

( * ) Notice: Subject to any disclaimer, the term of this patent is extended or adjusted under 35 U.S.C. 154(b) by 1420 days.

(21) Appl. No.: 11/445,015

(22) Filed: Jun. 1, 2006

(65) Prior Publication Data

US 2007/0282255 A1     Dec. 6, 2007

(51) Int. Cl.
*A61M 29/00*     (2006.01)
(52) U.S. Cl. .............. 604/101.01; 604/103.08
(58) Field of Classification Search .......... 604/918, 604/103.03, 103.07, 103.06, 102.01, 103.08, 604/103.01, 101.03, 101.01
See application file for complete search history.

(56) References Cited

U.S. PATENT DOCUMENTS

| | | | | |
|---|---|---|---|---|
| 3,635,223 A | * | 1/1972 | Klieman | 606/194 |
| 4,753,637 A | * | 6/1988 | Horneffer | 604/509 |
| 5,021,045 A | | 6/1991 | Buckberg et al. | |
| D335,705 S | | 5/1993 | Buckberg et al. | |
| 5,226,427 A | | 7/1993 | Buckberg et al. | |
| 5,423,745 A | * | 6/1995 | Todd et al. | 604/500 |
| 5,584,803 A | * | 12/1996 | Stevens et al. | 604/6.16 |
| 6,913,601 B2 | | 7/2005 | St. Goar et al. | |
| 6,928,313 B2 | | 8/2005 | Peterson | |

OTHER PUBLICATIONS

Edwards Research Medical Product Catalog (69 pages), relevant pp. 24-32, copyright 2005.
*Edwards Research Medical Product Catalog*; 2005.

\* cited by examiner

*Primary Examiner* — Kevin C Sirmons
*Assistant Examiner* — Deanna K Hall
(74) *Attorney, Agent, or Firm* — Senniger Powers LLP

(57) ABSTRACT

A medical device for performing a surgical procedure on a patient including an elongate tubular shaft having an outer surface extending from a proximal end to a distal end and an inner passage in fluid communication with a fluid source during use of the device. The shaft further has a lateral hole in the outer surface in fluid communication with the inner passage for delivering fluid from the device in a lateral direction during surgery. The device further includes a distal balloon having an exterior surface connected to the shaft and a projection extending from the exterior surface. The device also includes a proximal balloon connected to the shaft between the distal end and the proximal end of the shaft and a locating structure connected to the shaft. The hole is positioned in the outer surface between the distal balloon and the proximal balloon.

17 Claims, 6 Drawing Sheets

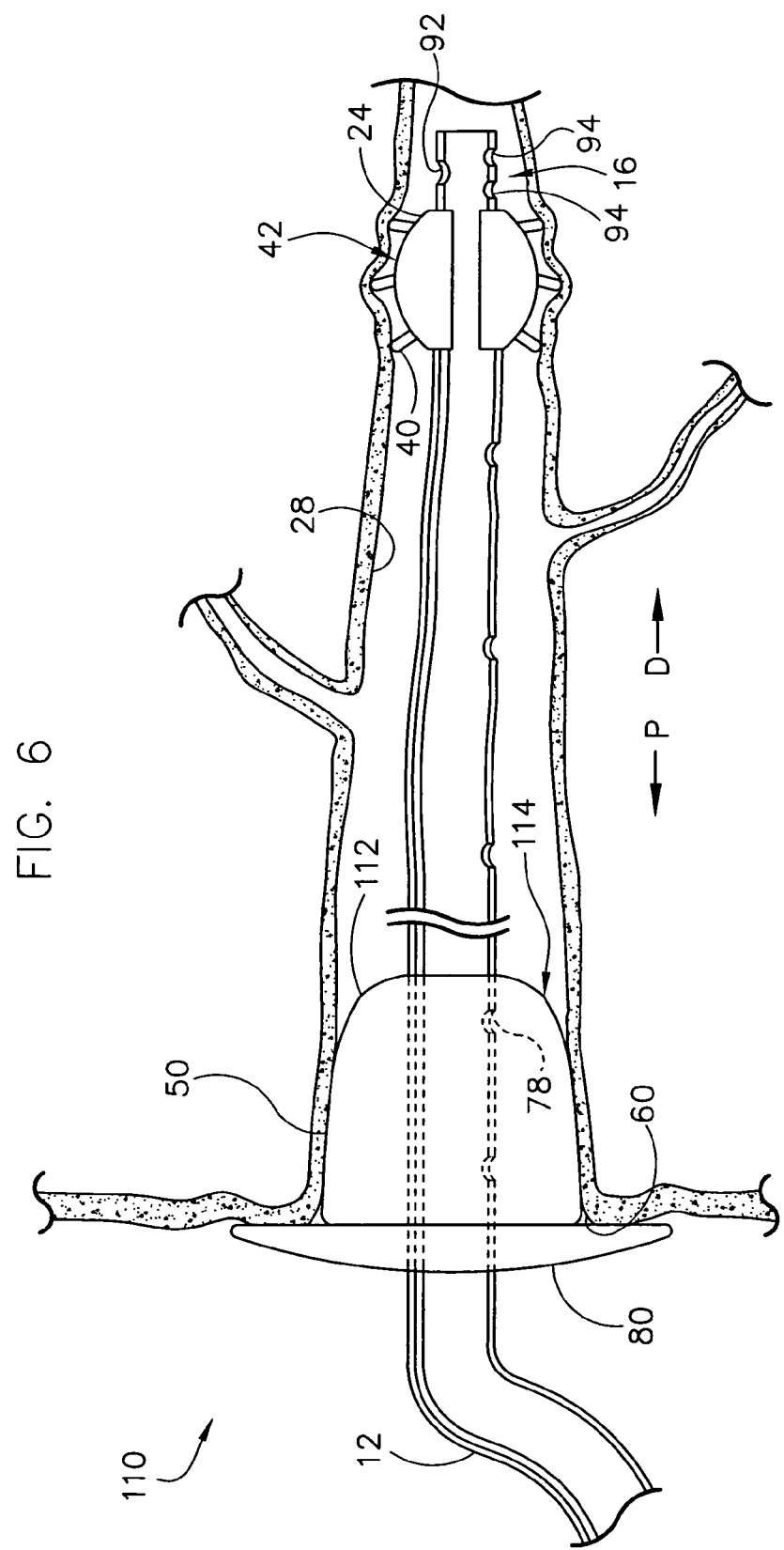

SELF-RETAINING AND FLUID DELIVERY CATHETER

BACKGROUND OF THE INVENTION

The present invention relates to a surgical catheter and, more particularly, to a catheter that can be self-retained in a cavity of a patient and deliver fluid to the cavity.

Performing surgical procedures on patients using a catheter sometimes requires that the catheter be secured in a desired position within the patient. Even when securing the catheter in a position within the patient is not necessary, securing the catheter often facilitates procedures. Activities requiring or facilitated by securing a catheter in position include deploying surgical instruments and delivering fluid or other material to the patient. As one particular example, cardioplegic fluid is often delivered to the heart muscle or myocardium of the patient during heart surgery. Cardioplegic fluid is a solution introduced to the heart during heart surgery to temporarily arrest the heart in a diastolic or relaxed state so the surgeon can more easily perform the surgery.

During heart operations, the patient is often placed on a cardiopulmonary bypass machine that performs the functions of the heart and lungs. While on the cardiopulmonary bypass, blood flowing toward the heart and lungs is diverted to the bypass machine. The bypass machine oxygenates the blood and pumps it back into the patient to ensure the other organ systems receive sufficient oxygenated blood. The heart, being deprived of blood, must be protected from damage. One conventional method of protecting the heart is to perfuse the myocardium with cardioplegic fluid. Temporarily arresting the heart using cardioplegic fluid and diverting blood flow away from the heart allows surgical operation on substantially bloodless and motionless heart chambers, surfaces, and related tributaries.

Cardioplegic fluid can be delivered to the myocardium in an antegrade or retrograde fashion. Antegrade delivery involves injecting the aorta or the coronary arteries directly with cardioplegic fluid so it travels along the path of normal blood flow to the heart muscle. Retrograde or reverse delivery involves injecting cardioplegic fluid into the coronary sinus, through which blood normally drains into the right atrium.

There are many situations when retrograde delivery is complimentary or preferable to antegrade delivery. Patients with significant obstruction in the coronary arteries (i.e., those undergoing heart bypass surgery) may receive insufficient cardioplegia when it is delivered in an antegrade fashion. Patients with an incompetent aortic valve cannot receive cardioplegia in an antegrade fashion unless the aorta is opened and the cardioplegia is delivered directly to the coronary orifices. This results in longer operations and creates a risk of bleeding from an aortic suture line or damage to the coronaries themselves. Further, delivering cardioplegia in a retrograde fashion during some procedures, such as during replacement or repair of the aortic or mitral valves, protects the heart without interrupting the procedure to deliver cardioplegia in an antegrade fashion. Without these interruptions, cardiopulmonary bypass time and the duration of the cardiac arrest are decreased.

Despite the potential advantages of retrograde delivery of cardioplegia, drawbacks in conventional catheter design often result in inefficient and/or ineffective delivery. One drawback of conventional catheters is that it is difficult to keep them positioned in the sinus. Successful retrograde cardioplegia delivery requires that a fluid delivering end of the feed catheter remains securely positioned in the coronary sinus during fluid delivery. Some conventional catheters include a balloon at a distal end of the catheter for securing the catheter in the coronary sinus so cardioplegic fluid can be repeatedly and accurately delivered. These distal balloons have proven ineffective for securing the catheter in the sinus because the balloons often slip along the inner surface of the sinus. In this way, the catheter can become dislodged from the sinus. The likelihood of the catheter being dislodged is increased due to the tapering structure of the coronary sinus, which tends to push the balloon proximally toward the orifice of the sinus.

Because of the likelihood of dislodgement and an inability for surgeons to know the catheters exact position, catheters are often inserted as far as possible into the coronary sinus for cardioplegic fluid injection. Inserting a catheter too far into the coronary sinus may perforate the sinus. Inserting the catheter too far into the sinus also prevents cardioplegic fluid from flowing into more proximal tributaries of the sinus and allows the proximal tributaries to serve as runoff paths from the heart muscle. As a further drawback of conventional catheters, cardioplegic fluid delivered into the sinus sometimes flows out of the sinus in a proximal direction (i.e., into the right atrium of the patient's heart). A catheter is needed that can be predictably positioned and securely retained in a cavity such as a coronary sinus and deliver fluid into distal and proximal portions of the cavity.

BRIEF SUMMARY OF THE INVENTION

The present invention relates to a medical device for performing a surgical procedure on a patient including an elongate tubular shaft. The shaft has an outer surface extending from a proximal end to a distal end and an inner passage in fluid communication with a fluid source during use of the device. The shaft further has a lateral hole in the outer surface in fluid communication with the inner passage for delivering fluid from the device in a generally lateral direction relative to the shaft during surgery. The device further includes a distal balloon having an exterior surface and an interior surface opposite the exterior surface connected to the shaft. The device also includes at least one projection extending outward from the exterior surface of the distal balloon positioned to engage tissue of the patient to retain the shaft in a desired position within the patient when the distal balloon is inflated during surgery. In addition, the device includes a proximal balloon connected to the shaft between the distal balloon and the proximal end and a locating structure connected to the shaft for locating the shaft in the desired position in the patient during use of the device. The locating structure is shaped and positioned on the shaft to keep the shaft from moving in a distal direction by engaging tissue of the patient when the shaft is in the desired position during surgery. The lateral hole is positioned in the outer surface of the shaft between the distal balloon and the proximal balloon.

In another aspect, the present invention relates to a medical device for performing a surgical procedure on a patient including an elongate tubular shaft. The shaft has an outer surface extending from a proximal end to a distal end and an inner passage in fluid communication with a fluid source during use of the device. The device further includes a balloon connected to the shaft for retaining the shaft in a desired position within the patient when the balloon is inflated during surgery. The balloon has an exterior surface and an elongate projection extending outward from the exterior surface of the balloon positioned to engage tissue of the patient when the distal balloon is inflated during surgery to retain the shaft in the desired position. The projection has a base adjacent the exterior surface of the balloon and a tip opposite the base and the tip is closer to the proximal end of the shaft than the base.

In yet another aspect, the present invention relates to a medical device for performing a surgical procedure on a patient including an elongate tubular shaft. The shaft has an exterior surface extending from a proximal end to a distal end and an inner passage in fluid communication with a fluid source during use of the device. The shaft further has a plurality of holes in the outer surface of the shaft in fluid communication with the inner passage for delivering fluid from the device in a generally lateral direction relative to the shaft during surgery. The device further includes a distal balloon connected to the shaft adjacent the distal end having an exterior surface for retaining the shaft in a desired position within the patient by engaging tissue of the patient when the shaft is positioned in a desired location and the distal balloon is inflated during surgery. At least one hole of the plurality of holes is positioned between the distal balloon and the proximal end.

In still another aspect, the present invention relates to a medical device for performing a surgical procedure on a patient including an elongate tubular shaft extending from a proximal end to a distal end. The medical device further includes a balloon connected to the shaft and a locating structure connected to the shaft proximal to the balloon for locating the shaft in the desired position in the patient during use of the device. The locating structure is shaped and positioned on the shaft to keep the shaft from moving in a distal direction by engaging tissue of the patient when the shaft is in the desired position during surgery.

In yet still another aspect, the present invention relates to a method for delivering fluid to a patient when performing a surgical procedure on the patient by way of a medical device including a shaft having an outer surface extending from a proximal end to a distal end, a distal balloon having an exterior surface connected to the shaft adjacent the distal end, a proximal balloon having an exterior surface connected to the shaft between the distal balloon and the proximal end of the shaft, an elongate projection extending outward from the exterior surface of the distal balloon, a hole positioned in the outer surface of the shaft between the distal balloon and the proximal balloon, and a locating structure connected to the shaft. The method includes guiding the distal end of the shaft to a desired position within the patient and ensuring the distal end is in the desired position by engaging the locating structure with tissue of the patient. The method further includes inflating the distal balloon to engage the elongate projection with tissue of the patient to secure the shaft in the desired position. The method also includes inflating the proximal balloon to engage the exterior surface of the proximal balloon with the tissue of the patient to retain fluid within a cavity in the patient defined in part by the proximal balloon and the distal balloon. In addition, the method includes delivering fluid into the cavity of the patient through the hole in the shaft.

In a further aspect, the present invention relates to a method for securing a medical device in a desired position within a patient when performing a surgical procedure on the patient wherein the device includes a shaft extending from a proximal end to a distal end, a distal balloon having an exterior surface connected to the shaft adjacent the distal end of the shaft, and an elongate projection extending outward from the exterior surface of the distal balloon. The method comprises guiding the distal end of the shaft to the desired position within the patient. The method further includes inflating the distal balloon to engage the elongate projection with tissue of the patient to secure the shaft in the desired position.

In another aspect, the present invention relates to a method a method for delivering a fluid into a patient during a surgical procedure on the patient by way of a medical device including an elongate tubular shaft having an outer surface extending from a proximal end to a distal end, a distal balloon having an exterior surface connected to the shaft adjacent the distal end, and at least one hole in the outer surface of the shaft between the distal balloon and the proximal end of the shaft. The method includes guiding the distal end of the shaft to a desired position within the patient and inflating the distal balloon to engage the exterior surface of the balloon with tissue of the patient to secure the shaft in the desired position. The method further includes delivering fluid into the patient through the hole in the shaft proximal to the distal balloon.

In yet another aspect, the present invention relates to a method for securing a medical device in a desired position within a patient when performing a surgical procedure on the patient wherein the device includes a shaft extending from a proximal end to a distal end, a balloon having an exterior surface connected to the shaft, and a disk connected to the shaft between the balloon and the proximal end. The method includes guiding the distal end of the shaft to the desired position within the patient and ensuring the distal end is in the desired position by engaging the disk with tissue of the patient. The method further includes inflating the balloon to engage the exterior surface of the balloon with tissue of the patient to secure the shaft in the desired position.

Other aspects of the present invention will be in part apparent and in part pointed out hereinafter.

BRIEF DESCRIPTION OF THE DRAWINGS

FIG. 6 is a cross section similar to FIG. 5 shown with the distal balloon and a proximal balloon inflated.

Corresponding reference characters indicate corresponding parts throughout the several views of the drawings.

DETAILED DESCRIPTION OF THE INVENTION

Figure 1:
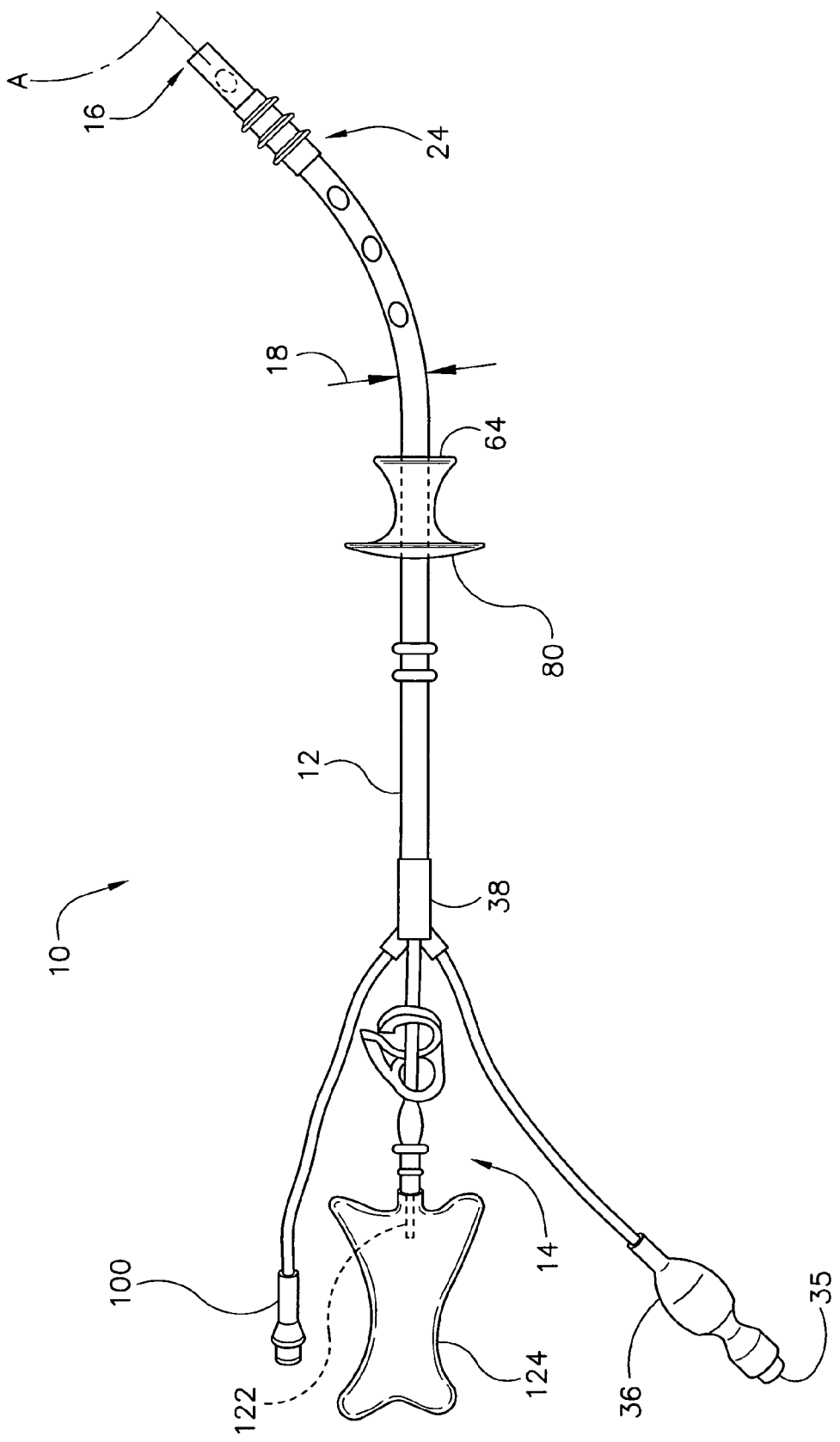
FIG. 1 is a top plan of a medical device according to a first embodiment of the present invention.

Referring to the figures, and more particularly to FIG. 1, a medical device according to a first embodiment of the present invention is designated in its entirety by reference number 10. The medical device 10 is used for performing a surgical procedure on a patient. Although the device 10 may be used to perform other surgical procedures, in one embodiment the device is used to deliver cardioplegic fluid in a retrograde fashion through a coronary sinus of the patient. The medical device 10 includes an elongate tubular body or shaft 12 extending from a proximal end 14 to a distal end 16. The shaft 12 may be made of various materials without departing from the scope of the present invention. For example, in one embodiment, the shaft 12 is made of polyurethane. Although the shaft 12 may have other lengths without departing from the scope of the present invention, in one embodiment the shaft has a length of between about 27 cm and about 32 cm.

Although the shaft 12 may have other outer diameters 18 without departing from the scope of the present invention, in one embodiment the shaft has an outer diameter of between about 4 mm and about 4.7 mm. The shaft 12 has at least one interior channel 20 (shown in FIG. 2) extending between the proximal end 14 and the distal end 16. Although the interior channel 20 may have other diameters 22, in one embodiment the interior channel has a diameter of between about 2 mm and about 4 mm. The interior channel 20 can transport a variety of surgical instruments (not shown) and materials.

Figure 2:
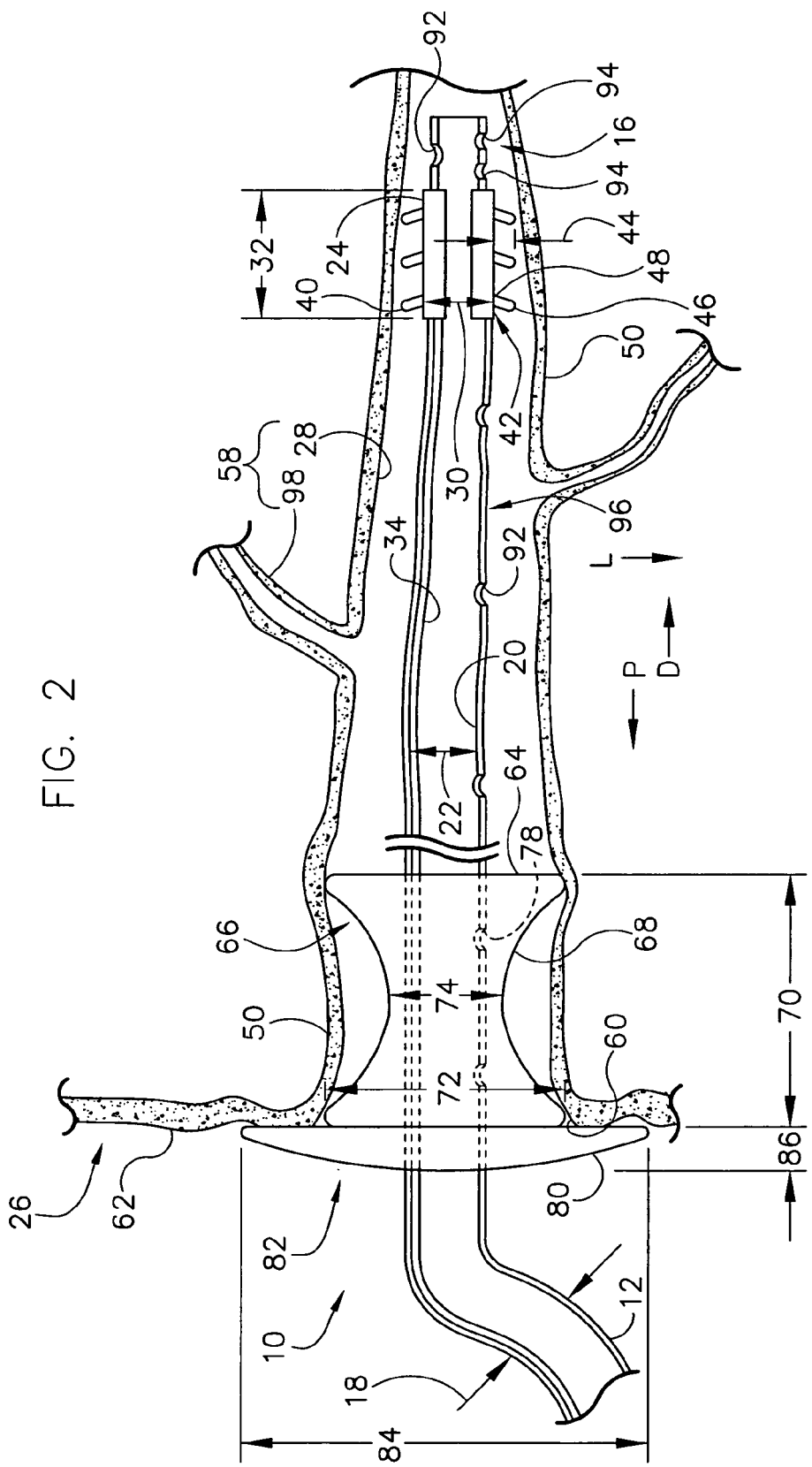
FIG. 2 is a cross section of a distal end of the medical device according to the first embodiment within a patient.
Figure 3:
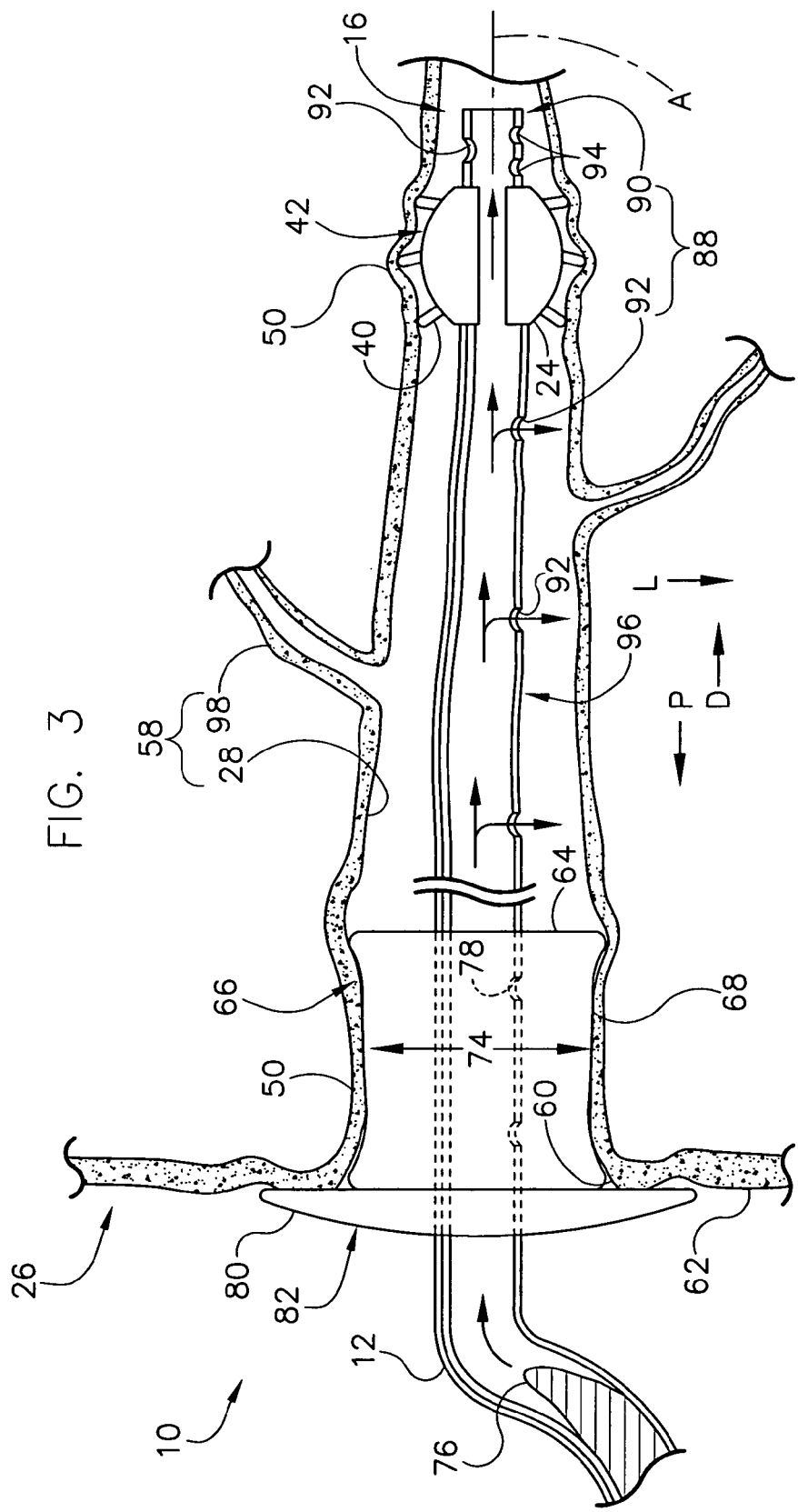
FIG. 3 is a cross section similar to FIG. 2 shown with a distal balloon and a proximal balloon inflated and fluid passing from the device.

As shown in FIGS. 1 and 2, the device 10 further includes a distal balloon 24 connected to the shaft 12 adjacent the distal end 16 of the shaft. As shown in FIG. 3, the distal balloon 24 retains the shaft 12 in a desired or predetermined position within the patient 26 when the distal balloon is inflated during surgery. Specifically, the distal balloon 24 engages a lumen or cavity 28, such as the coronary sinus, of the patient 26 when the shaft 12 is properly positioned in the cavity and the distal balloon is inflated to retain the shaft 12 in the lumen or cavity. The retention provided by the distal balloon 24 is especially useful when the shaft 12 is positioned in a tapered cavity 28. For example, devices inserted into cavities 28 that generally decrease in size in a proximal direction "P", as shown in FIG. 2, are urged in a distal direction "D" by interaction between the walls of the cavity and the device.

The device 10 is said to be self-retaining because it can retain itself in a position in the cavity 28 and does not require auxiliary equipment or clamps to stay in position. The distal balloon 24 may have various shapes and sizes without departing from the scope of the present invention. In one embodiment, the distal balloon 24 is generally cylindrical, has an outer diameter 30 of between about 5 mm and about 6 mm, and a length 32 of between about 15 mm and about 25 mm when it is deflated, as shown in FIG. 2. In this embodiment, the distal balloon 24 has an outer diameter 30 of between about 18 mm and about 24 mm when it is inflated. Although the distal balloon 24 may be made of various materials without departing from the scope of the present invention, in one embodiment, the distal balloon 24 is made of polyurethane or silicone. The distal balloon 24 is connected to a fluid source (not shown), such as a source of saline or air, for selectively inflating the distal balloon by way of a distal line 34 and a balloon inflation port 35 (shown in FIG. 1). The balloon inflation port 35 is connected to the distal line 34 and may be an integral part of the device 10, connecting to the shaft at a connector 38, or a separate component inserted through the connector. The distal line 34 extends through the interior channel 20 of the shaft 12 from the proximal end 14 to the distal balloon 24. In one embodiment, the distal line 34 extends outside of the shaft from the fluid source or balloon inflation port 35 to the balloon 24. The distal balloon 24 may be inflated and deflated manually or automatically. Pressure within the distal balloon 24 can be measured using a distal balloon pressure gauge connected to the distal line 34. For example, the device 10 may include or be used in combination with a syringe connected to the distal line 34 including a handheld bladder 36. The user could use the bladder 36 to determine pressure in the distal balloon 24 by, for example, manually feeling the bladder. In one embodiment, a predetermined volume of inflation fluid is delivered to the distal balloon 24 during the surgery. The predetermined volume of inflation fluid may be dependant on various factors, such as the size of the patient's cavity 28.

In one embodiment, at least one projection 40 extends from an outer surface 42 of the distal balloon 24. The projections 40 may be formed integrally with the distal balloon 24 or formed separately from and then mounted on the distal balloon. The projections 40 may have various sizes and shapes without departing from the scope of the present invention. Generally, the projections 40 are sized and shaped to effectively engage tissue of the patient to secure the device 10 in a desired or predetermined position by preventing the shaft 12 from moving in the proximal direction "P" (i.e., towards removing the shaft from the patient). In one embodiment, the distal balloon 24 and any projections 40 that may extend from it are sized and shaped so that they do not completely block the cavity 28 in which they are securing the shaft 12. In this way, fluid being delivered from the shaft 12 on either side of the distal balloon 24 can flow around the distal balloon to the other side. In one embodiment, each projection 40 has a finger-like cross-sectional shape. Each projection 40 may extend continuously around the entire outer surface 42 of the distal balloon 24 (i.e., as ribs) as shown in the figures or the projections may be distributed around the balloon (i.e., as fingers). It is contemplated that each projection 40 may extend continuously around a portion of the outer surface 42, such as extending continuously around between about 5% and about 25% of a circumference of the outer surface.

In one embodiment, each projection 40 extends above the outer surface 42 of the distal balloon 24 by a distance 44 of between about 1.5 mm and about 3.0 mm. In one embodiment, the distance 44 by which each projection 40 extends above the outer surface 42 is between about 10% and about 65% of the outer diameter 30 of the distal balloon 24. In this embodiment, projection 40 sizes within this range are especially effective for retaining the shaft 12 in the desired position. Projections 40 sized much smaller than this range may not effectively hold the shaft 12 from moving in the proximal direction "P". Further, in one embodiment each projection 40 has a thickness of between about 0.5 mm and about 1.0 mm. As shown in FIGS. 2 and 3, each projection 40 may be shaped and connected to the distal balloon 24 so that a tip 46 of the projection is generally proximal to a base 48 of the projection (i.e., the projection is proximally oriented) when the shaft 12 is positioned in the desired location and the distal balloon is deflated and/or inflated so the projection acts as a barb to prevent movement in the proximal direction P. That is, each projection 40 may extend generally outward and generally laterally from the outer surface 42 of the distal balloon 24. As shown in FIG. 3, the projections 40 engage tissue 50 of the patient 26 when the distal balloon 24 is inflated. A material and the size (including thickness and distance 44 from the outer surface 42 of the distal balloon 24) of the projections 40 may be selected so the projections securely engage the cavity 28 walls and prevent proximal movement.

Figure 4:
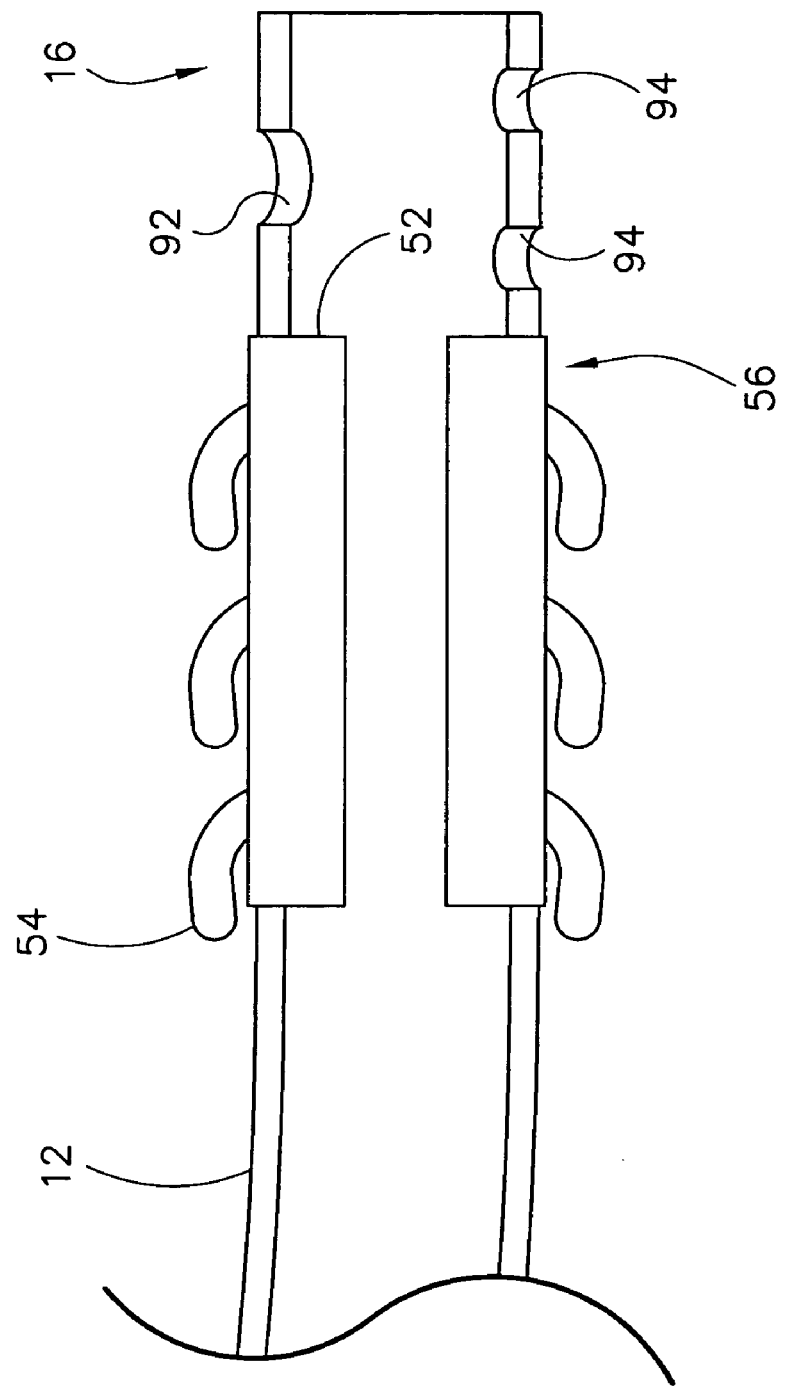
FIG. 4 is a cross section of an alternate embodiment of projections connected to the distal balloon.

FIG. 4 shows an embodiment of a distal balloon 52 and connected projections 54 that lay generally flat against the distal balloon surface 56 when the balloon is deflated. The projections 54 of this embodiment rise to an engaging position, similar to the engaging position of the projections 40 shown in FIG. 3, when the balloon 52 is inflated. Projections 40, 54 that can lay generally flat when the balloon 24, 56 are deflated and assume an engaging position when the balloon is inflated facilitate guiding the device 10 through the patient by avoiding unwanted contact between the projections and the patient and engaging patient tissue 48 when needed to secure the device in the desired position. In one embodiment (not shown), each projection 40, 54 has a tapered cross-sectional shape, such as generally triangular, so that the tip is thinner than the base so the tip can flex when it contacts the tissue 50 and the base is more firmly connected to the distal balloon surface 40, 56. Such tapered projections may lay generally against or close to the balloon 24, 52 when the balloon is deflated as described above.

Although the medical device 10 may be used in other applications, the tissue 50 shown in FIGS. 2 and 3 may be part of the coronary sinus of the patient's heart. The coronary sinus includes a venous system 58 and an ostium or orifice 60. During normal heart function, blood fed to the muscles of the heart is drained from those muscles into the right atrium 62 of the heart by way of the coronary sinus. Using the device 10, fluid such as cardioplegic fluid can be sent to the heart muscle from a direction opposite to normal blood flow by delivering the fluid into the coronary sinus.

The medical device 10 further includes a proximal balloon 64 connected to the shaft 12 proximal to the distal balloon 24. The proximal balloon 64 works with the distal balloon 24 to retain the shaft 12 in the desired position when both balloons are inflated. The proximal balloon 64 has an outer surface 66 that engages patient tissue 50 when the proximal balloon is inflated. By engaging patient tissue 50 adjacent the orifice 60, the proximal balloon biases the shaft 12 in the proximal direction "P" with respect to the coronary sinus. At the same time, the inflated distal balloon 24 holds the shaft 12 in place in the sinus thereby creating a tension between the distal balloon and the proximal balloon 64. In this way, the balloons 24, 64 work together to hold the shaft 12 in the desired position in the sinus and create a strong seal at the orifice 60 using the proximal balloon. The inflated proximal balloon 64 may also provide supplementary retention for the device 10 when the distal balloon 24 is also inflated. The retention provided by either or both of the balloons 24, 64 minimizes the likelihood of unwanted proximal dislodgement of the shaft 12 from the cavity 28 in which it is positioned. The proximal balloon 64 may be made of various materials without departing from the scope of the present invention. For example, in one embodiment, the proximal balloon 64 is made of polyurethane or silicone.

As shown in FIG. 3, the proximal balloon 64 is shaped to engage a portion of the patient 26 when the proximal balloon is inflated during surgery. As shown in FIG. 2, the proximal balloon 64 may be sized and shaped so that the proximal balloon contacts the patient 26 even when it is deflated. The proximal balloon 64 may have various shapes without departing from the scope of the present invention. In the embodiment shown in FIGS. 1-3, the proximal balloon 64 has a concave portion 68 when the proximal balloon is deflated. The concave portion 68 receives patient tissue 50 when the shaft 12 is in the desired position. For example, as shown in FIG. 2, the concave portion 68 receives tissue of the coronary sinus orifice 60. The proximal balloon 64 of this embodiment may have various sizes without departing from the scope of the present invention. Although the proximal balloon 64 may have other lengths 70 without departing from the scope of the present invention, in one embodiment the proximal balloon has a length of between about 20 mm and about 30 mm. Although the proximal balloon 64 may have other maximum outer diameters 72 when deflated, in one embodiment the proximal balloon has a maximum outer diameter of between about 20 mm and about 25 mm. Although the proximal balloon 64 may have other minimum outer diameters 74 without departing from the scope of the present invention, in one embodiment the proximal balloon has a minimum outer diameters of between about 12 mm and about 16 mm. When the proximal balloon 64 of this embodiment expands, as shown in FIG. 3, the minimum diameter 74 increases to between about 12 mm and about 16 mm and the maximum diameter 72 increases to between about 20 mm and about 25 mm. In one embodiment, the maximum diameter 72 and the minimum diameter 74 of the proximal balloon 64 remain substantially are substantially unchanged when the distal balloon 64 is inflated and deflated. In this embodiment, the proximal balloon 64 is easily deformable when deflated and more rigid or turgid when inflated to better hold its position adjacent the sinus orifice 60.

Although the proximal balloon 64 may be inflated in other ways without departing from the scope of the present invention, in one embodiment the proximal balloon is inflated using the same fluid 76 (shown in FIG. 3) being delivered to the patient 26 during the surgery. For example, the shaft 12 can include one or more inflation/deflation channels 78 adjacent the proximal balloon. The fluid automatically flows through the channels 78 when fluid 76 moves past the proximal balloon 64 as it is being delivered through the shaft 12 because of pressure gradients the fluid encounters within the shaft. In this embodiment, the proximal balloon 64 will automatically inflate whenever fluid 76 is being delivered to the patient 26 and will deflate when the fluid is not being delivered. The device 10 may be configured so the proximal balloon 64 is manually inflated and deflated. For example, in one embodiment (not shown), the proximal balloon 64 is connected to a fluid source, such as a source of saline or air, for selectively inflating the proximal balloon. For this embodiment, the proximal balloon may be inflated through the same inflation port 35 used to inflate the distal balloon 24 or a different port. Pressure within the proximal balloon 64 can be measured using the same hand-held bladder 36 used for the distal balloon 24.

The medical device 10 may also include a locating structure 80 that is relatively rigid (e.g., compared to the most flexible portion of the proximal balloon 64) positioned on the shaft 12 for locating the shaft in the desired position in the patient 26. As shown in FIG. 1, the structure 80 may include a disk connected to the shaft 12 adjacent and proximal to the proximal balloon 64 for locating the shaft in the desired position in the patient 26. The disk 80 may be connected to the proximal balloon 64. The disk 80 is shaped and positioned on the shaft 12 to keep the shaft from moving in the distal direction "D" by engaging tissue 50 of the patient 26 when the shaft is in the desired position during surgery. In one embodiment, the relatively rigid structure 80 includes a portion (not shown in detail but similar to the size, shape, and location of the disk. 80 shown in FIG. 1) of the proximal balloon 64 adjacent a proximal end of the proximal balloon. The proximal balloon 64 may be inserted into the orifice 60 until the locating structure 80 engages the orifice. The locating structure 80 is sized and shaped and has a rigidity so as to prevent easy insertion of the shaft 12 into the cavity beyond the desired position. When the locating structure 80 engages the orifice 60, the user will know the shaft 12 has been properly positioned in the cavity 28 from the tension they sense as a result of the locating structure resisting entry into the cavity. In one embodiment, the locating structure 80 ensures that the proximal balloon 64 does not block or occlude any tributaries (referenced as 98 in FIGS. 2 and 3) from the primary cavity 28 when the shaft 12 is positioned in the desired location and the proximal balloon 64 is inflated to limit distal insertion of the shaft beyond the desired position. Ensuring the proximal balloon 64 does not block tributaries is especially helpful for delivering fluid to more proximal tributaries of the cavity 28, which often get blocked by conventional fluid delivery devices.

When the device 10 is positioned in the patient as desired, the disk 80 and/or the proximal balloon 64 may be used to block cardioplegic fluid from exiting the cavity 28 through the sinus orifice 60. In one embodiment, the device 10 is configured so the proximal balloon 64 becomes only slightly positioned within the cavity 28. In this way, the proximal balloon 64 and/or disk 80 can block cardioplegic fluid from exiting the cavity 28 through the sinus orifice 60 but not block the fluid from entering any tributaries leading to the heart muscle from the cavity 28 at the far proximal end adjacent the orifice.

The disk 80 may have various shapes without departing from the scope of the present invention. For example, the disk 80 may be generally round and have a convex surface 82. Although the disk 80 may have other diameters 84 (shown in FIG. 2) without departing from the scope of the present invention, in one embodiment the disk has a diameter of between about 20 mm and about 25 mm. Although the disk 80 may have other maximum thicknesses 86 without departing from the scope of the present invention, in one embodiment the disk has a maximum thickness of between about 1 mm and about 3 mm. Although the disk may be made of other materials without departing from the scope of the present invention, in one embodiment the disk is made of silicone.

Once the medical device 10 is located within the patient 26 as desired using the proximal balloon 64 and/or the locating disk 80, the medical device 10 can be secured to the patient and used to perform various procedures. As shown in FIG. 3, the medical device 10 further includes one or more holes 88 in the shaft 12 for deploying surgical instruments (not shown) and/or delivering fluid 76 to the patient 26. The holes 88 are in fluid communication with a fluid source (not shown). For example, the cardiopulmonary bypass machine (not shown) that may be connected to the device 10 may include a fluid 76 containing reservoir and associated pump for supplying fluid to the shaft and holes 88. Although the fluid source can be connected to the shaft 12 at other places, in one embodiment, the fluid source is connected to the shaft at the proximal end 14. The holes 88 may include a distal hole 90 through which instruments can be deployed and fluid 76 can be delivered from the shaft 12 generally along an axis "A" of the shaft. Deploying instruments and delivering fluid 76 in a generally axial direction relative to the shaft 12 allows the instruments and fluid to more easily reach positions in the cavity 28 distal to the shaft. As shown in FIG. 2, the shaft 12 may extend beyond the distal balloon 24 and terminate at the distal hole 90.

The shaft holes 88 may also include one or more side holes 92 in an outer surface 96 of the shaft 12. These side holes 92 allow fluid 76 to be delivered out of the device 10 in a generally lateral direction "L" of the shaft 12 during surgery. Although the side holes 92 may be positioned in various locations along the shaft 12, in one embodiment the side holes are positioned between the distal balloon 24 and the proximal balloon 64 and between the distal balloon and the distal end 16 of the shaft 12. The side holes 92 may have the same or various sizes without departing from the scope of the invention. For example, as shown in FIGS. 2-6, side holes 92 adjacent the distal end 16 of the shaft 12 may include one or more holes 94 that are smaller than the other side holes. Side holes 92 facilitate introduction of fluid 76 to portions of the patient 26 that are lateral to the shaft 12, such as tributaries 98 from the cavity 28 in which the shaft is disposed. Holes 92, 94 on both sides of the distal balloon 24 also allows blood and/or cardioplegia to flow to or from the coronary sinus without deflating the distal balloon. For example, the holes 92, 94 on both sides of the distal balloon 24 allow blood to drain from the coronary sinus when cardioplegia is being delivered in an antegrade fashion without deflating the distal balloon. In conventional catheters having securing balloons, the balloon must be deflated to drain the coronary sinus. The current device 10, on the other hand, allows the user to selectively switch between providing cardioplegia in an antegrade fashion and a retrograde fashion without deflating the distal balloon 24.

As described above, the disk 80 and/or the proximal balloon 64 can be used to locate the device 10 in a desired location and to block fluid 76 from moving proximally out of the cavity 28. For example, the proximal balloon 64 can block fluid 76 from leaving the cavity 28 by inflating with fluid to fill the cavity orifice 60 whenever the fluid is being delivered through the holes 88.

As shown in FIG. 1, the device 10 may further include a cavity pressure gauge 100 for determining a pressure within the cavity 28 (shown in FIGS. 2 and 3). The cavity pressure gauge 100 can be connected to the cavity by way of a pressure line (not shown) and an opening (not shown) adjacent the distal end 16 of the shaft 12. The cavity pressure gauge 100 can be used to determine the pressure within the cavity 28 when fluid 76 is being delivered to the patient 26. In this way, the user can determine whether insufficient, sufficient, or too much fluid 76 has been administered to the patient 26 and/or whether the proximal balloon 64 is properly sealing the sinus orifice 60.

Figure 5:
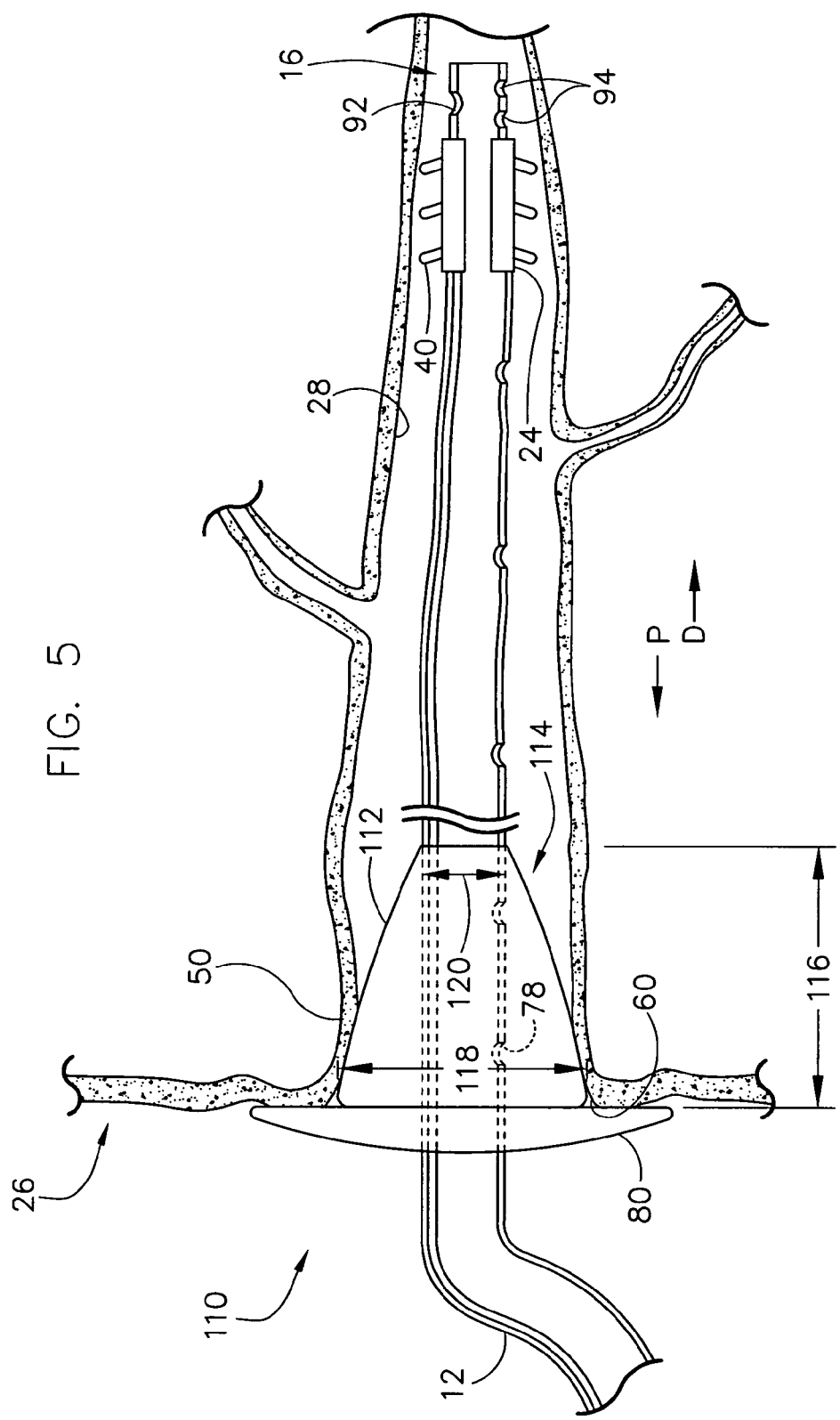
FIG. 5 is a cross section of a distal end of a medical device according to a second embodiment of the present invention within the patient.

FIG. 5 shows a medical device 110 according to a second embodiment of the present invention. This embodiment includes a proximal balloon 112 that is generally conical when the balloon is deflated and/or inflated. The proximal balloon 112 may be configured so that it contacts the patient 26 when the shaft 12 is guided to the desired location and the proximal balloon is deflated. When the proximal balloon 112 is inflated, as shown in FIG. 6, the proximal balloon engages the tissue 48 of the patient 26 with an outer surface 114 of the balloon. As with previous embodiments, the proximal balloon 112 of this embodiment works with the distal balloon 24 to retain the shaft 12 in the desired position when both balloons are inflated. By engaging the tissue 50 inside the cavity 28 adjacent the orifice 60, the proximal balloon biases the shaft 12 in the proximal direction "P" with respect to the coronary sinus. This biasing force is fostered at least in part by the conical shape of the proximal balloon 112. At the same time that the proximal balloon 112 is biasing the shaft 12 in the proximal direction, the inflated distal balloon 24 holds the shaft 12 in place in the sinus thereby creating a tension between the distal balloon and the proximal balloon 112. In this way, the balloons 24, 112 work together to hold the shaft 12 in the desired position in the sinus and create a strong seal at the orifice 60 of the sinus using the proximal balloon. The inflated proximal balloon 112 may also provide supplementary retention for the device 10 when the distal balloon 24 is also inflated. The retention provided by either or both of the balloons 24, 112 minimizes the likelihood of unwanted proximal dislodgement of the shaft 12 from the cavity 28 in which it is positioned.

The proximal balloon 112 of this embodiment may have various sizes without departing from the scope of the present invention. Although the proximal balloon 112 may have other lengths 116 without departing from the scope of the present invention, in one embodiment the proximal balloon has a length of between about 20 mm and about 30 mm. Although the proximal balloon 112 may have other maximum diameters 118 without departing from the scope of the present invention, in one embodiment the proximal balloon has a maximum diameter of between about 20 mm and about 25 mm when deflated and a maximum diameter of between about 20 mm and about 25 mm when inflated. Although the proximal balloon 112 may have other minimum diameters 120 without departing from the scope of the present invention, in one embodiment the proximal balloon 112 has a minimum diameter of between about 10 mm and about 15 mm when deflated and a minimum diameter of between about 10 and about 15 when inflated. As described above regarding proximal balloons according to other embodiments, the maximum diameter and the minimum diameter of the proximal balloon may remain substantially unchanged when the balloon is inflated and deflated and the proximal balloon may be easily deformable when deflated and more rigid or turgid when inflated to better hold its position adjacent the sinus orifice 60. The medical device 110 according to the second embodiment is otherwise identical to the medical device 10 of the first embodiment and therefore will not be described in further detail.

The medical device 10, 110 may include or be used in combination with various movement control mechanisms. For example, the device 10, 110 may include or be used in combination with a stylet 122. The stylet 122 is a stiff wire for inserting into the shaft 12 to maintain a shape of the shaft and assist the user in guiding the shaft through the patient 26. The stylet 122 may be connected to a handle 124 and inserted into the shaft 12 adjacent the proximal end 14. After the shaft 12 has been positioned within the patient 26 as desired, the user may remove the stylet 122 from the shaft. Removing the stylet 122 allows the user to connect other things to the shaft 12 where the stylet was connected, such as a fluid delivery line (not shown) connected to the bypass machine. A user guides the shaft 12 to a desired position in the patient 26 by controlling the shaft directly and/or by way of control mechanisms such as the stylet 122. As shown in FIGS. 2 and 5, guiding the shaft 12 to the desired location can include locating the shaft by engaging tissue 50 of the patient 26 using the disk 80 and/or the proximal balloon 64, 112. The disk 80 and/or proximal balloon 112 keep the device 10, 110 from being inserted too far into the cavity 28.

After the user has guided the distal end 16 of the shaft 12 to a desired position within the patient, the distal balloon 24, 52 and the proximal balloon 64, 112 are inflated to secure the shaft in the desired position. The distal balloon 24, 52 is inflated so that the outer surfaces 42, 56 and/or the projections 40, 54 extending therefrom engage tissue 50 of the patient 26 for fixing the shaft 12 in position in the cavity 28 (e.g., preventing the shaft from moving proximally in and from the cavity). After the distal balloon 24, 52 is inflated to secure the shaft 12 in place in the cavity 28, the proximal balloon 64, 112 is inflated to seal the orifice 60 of the coronary sinus orifice 60 so fluid delivered through the shaft 12 does not exit the sinus proximally (i.e., flow into the right atrium). The distal balloon 24, 52 and the proximal balloon 64, 112 work together to ensure the shaft 12 remains in position and fluid does not spill proximally from the cavity 28. For example, while the inflated distal balloon 24, 52 secures the shaft 12 from moving proximally in position, the inflating proximal balloon 64, 112 fills the orifice 60 and may bias the shaft toward moving proximally. Thus, if not for the anchoring effect of the inflated distal balloon 24, 52, the inflated proximal balloon 64, 112 might force the shaft 12 proximally in the cavity 28, which may weaken sealing between the proximal balloon and the sinus orifice 60. The configuration of the devices 10, 110 and described cooperation of the distal balloon 24, 54 and proximal balloon 64, 112 allow the shaft 12 to be securely positioned in the cavity 28 and the proximal orifice 60 to be sealed without lodging a balloon farther distally into the cavity. In other words, without a distal balloon 24, 54, a proximal balloon would have to be positioned farther within the cavity to seal the orifice 60. However, a more distally inserted proximal balloon would undesirably block the most proximal tributaries 98 of the venous system 58 and keep fluid 76 from entering them.

After the shaft 12 has been secured in the desired position, the user may continue with any of various surgical activities. For example, the user may guide surgical instruments or deliver fluid 76 along the shaft 12 and through the holes 88. As shown in FIG. 3, the user may deliver fluid 76 to the patient 26 in the generally distal "D" direction through the distal hole 90 and in the generally lateral "L" direction with respect to the shaft 12 through one or more of the side holes 92. Also, as described above, the device 10, 110, may be configured so the proximal balloon 64, 112 automatically inflates whenever fluid is delivered through the shaft 12 and to the patient 26. For example, in one embodiment, the same fluid 76 being delivered to the patient through the holes 92 may be directed to the proximal balloon 64, 112 to fill it. The device 10, 110 may also be configured so that the proximal balloon 64, 112 is filled manually. For example, in one embodiment (not shown in detail), the proximal balloon 64, 112 is connected to a fluid source, such as a saline bladder, which can be actuated manually to deliver fluid to the proximal balloon when desired.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical device for delivering fluid from a fluid source to a coronary passageway in a patient during a surgical procedure on the patient, the device comprising:

an elongate tubular shaft having an outer surface extending from a proximal end to a distal end, an inner passage in fluid communication with the fluid source during use of the device, and a lateral hole in the outer surface in fluid communication with the inner passage for delivering fluid from the device in a generally lateral direction relative to the shaft during surgery;

a distal non-sealing balloon connected to the shaft at a location distal to the lateral hole and having an exterior surface and an interior surface opposite the exterior surface;

a plurality of projections extending outward from the exterior surface of the distal non-sealing balloon, each of the projections having a base connected to the exterior surface of the distal non-sealing balloon and a tip opposite the base, the tip being positioned to engage an interior surface of the coronary passageway to retain the shaft in a desired position within the coronary passageway by preventing the shaft from moving in a proximal direction when the balloon is inflated during surgery, the tip of each projection being spaced from the corresponding base by a distance sufficient to maintain a space between the exterior surface of the distal non-sealing balloon and the interior surface of the coronary passageway permitting fluid flow between the exterior surface of the distal non-sealing balloon and the interior surface of the coronary passageway when the distal non-sealing balloon is inflated; and a proximal sealing balloon connected to the shaft between the lateral hole and the proximal end, the proximal sealing balloon having an exterior surface that engages and seals against the interior surface of the coronary passageway preventing flow past the proximal sealing balloon when inflated.

2. A medical device as set forth in claim 1 wherein each projection extends outward from the exterior surface by a distance that is between about 10% and about 65% of an outer diameter of the distal non-sealing balloon.

3. A medical device as set forth in claim 1 wherein said elongate tubular shaft has a longitudinal hole adjacent said distal end in fluid communication with said fluid source for delivering fluid from the device in a generally longitudinal direction relative to the shaft during surgery.

4. A medical device as set forth in claim 1 wherein the proximal sealing balloon has a generally tapered shape when inflated.

5. A medical device as set forth in claim 1 wherein the proximal sealing balloon has a concave portion when the proximal sealing balloon is deflated for receiving patient tissue when the shaft is in the desired position.

6. A medical device as set forth in claim 1 wherein:
said elongate tubular shaft has a plurality of holes in the outer surface of the shaft for delivering fluid from the device in a generally lateral direction relative to the shaft during surgery; and
at least one of said plurality of holes is positioned between said distal balloon and said proximal balloon.

7. A medical device as set forth in claim 1 further comprising a locating structure connected to the shaft for locating the shaft in the desired position in the coronary passageway of the patient by engaging coronary tissue of the patient during surgery.

8. A medical device as set forth in claim 7 wherein said locating structure includes a disk connected to the shaft between the proximal balloon and the proximal end of the shaft.

9. A medical device as set forth in claim 7 wherein said locating structure includes a portion of the proximal balloon having increased rigidity adjacent a proximal end of the proximal balloon.

10. A medical device for performing a surgical procedure on a patient comprising:
an elongate tubular shaft having a longitudinal axis, an outer surface extending from a proximal end to a distal end, and an inner passage in fluid communication with a fluid source during use of the device;
a balloon connected to the shaft for retaining the shaft in a desired position within the patient when the balloon is inflated during surgery, the balloon having an exterior surface and a plurality of elongate projections extending outward from the exterior surface of the balloon, the projections each having a base adjacent the exterior surface of the balloon and a tip opposite the base, the tips of the projections being positioned to engage tissue of the patient to retain the shaft in a desired position within the patient by preventing the shaft from moving in a proximal direction when the balloon is inflated during surgery, the tips being spaced sufficiently close to one another and being spaced sufficiently from the respective bases to space the exterior surface of the balloon from the tissue for permitting fluid flow past the balloon between the exterior surface and the tissue; and
wherein said tip is closer to the proximal end of the shaft than the base.

11. A medical device for delivering fluid from a fluid source to a coronary passageway in a patient during a surgical procedure on the patient, the device comprising:
an elongate tubular shaft having an outer surface extending from a proximal end to a distal end, an inner passage having an inlet adapted for fluid communication with the fluid source during use of the device, and a plurality of holes in the outer surface of the shaft, each of the holes being in fluid communication with the inlet of the inner passage for delivering fluid from the source to the coronary passageway in the patient during surgery;
a distal balloon connected to the shaft adjacent said distal end having an exterior surface;
a proximal balloon connected to the shaft between the distal balloon and the proximal end of the shaft;
wherein at least one hole of said plurality of holes is positioned between said distal balloon and the proximal balloon;
wherein at least one hole of said plurality of holes is positioned between said distal balloon and the distal end of the shaft; and
further comprising a plurality of elongate projections extending outward from the exterior surface of the distal balloon for engaging tissue in the coronary passageway of the patient, the elongate projections each having a base adjacent the exterior surface of the balloon and a tip opposite the base, the tip being positioned to engage tissue in the coronary passageway when the distal balloon is inflated during surgery to retain the shaft in said desired position by preventing the shaft from moving in a proximal direction, the tip being spaced from the base by a distance sufficient to maintain the exterior surface of the distal balloon spaced from and not in contact with the tissue, the elongate projections permitting flow along the coronary passageway between the external surface of the balloon and the tissue of the coronary passageway when the distal balloon is expanded in the passageway.

12. A medical device as set forth in claim 11 further comprising a locating structure connected to the shaft adjacent the proximal balloon for locating the shaft in the desired position in the patient by engaging tissue of the patient during surgery.

13. A method for delivering cardioplegic fluid into a coronary sinus extending from a right atrium of a patient by way of a medical device including a shaft having an outer surface extending from a proximal end to a distal end, a distal balloon having an exterior surface connected to the shaft adjacent said distal end, a proximal balloon having an exterior surface connected to the shaft between the distal balloon and said proximal end, an elongate projection extending outward from the exterior surface of the distal balloon, a plurality of projections each having a base connected to the exterior surface of the distal balloon and a tip opposite the base, a hole positioned in the outer surface of the shaft between the distal balloon and the proximal balloon, and a locating structure connected to the shaft, the method comprising:
guiding the distal end of the shaft into the coronary sinus;
ensuring the distal end is in the coronary sinus by engaging said locating structure with tissue in the right atrium around an ostium of the coronary sinus;
inflating the distal balloon to engage the tip of the elongate projection with tissue in the coronary sinus to secure the shaft in the desired position while maintaining the exterior surface of the distal balloon in a position spaced from and not in contact with the tissue to permit fluid flow through the coronary sinus past the distal balloon;
inflating the proximal balloon to engage the exterior surface of the proximal balloon with tissue in the coronary sinus adjacent the ostium to seal against the coronary sinus to retain fluid within the coronary sinus; and delivering fluid into the coronary sinus to a position in the coronary sinus distal to the distal balloon by delivering fluid through the hole in the shaft between the proximal and distal balloons and permitting the fluid to pass through the coronary sinus between the tissue of the coronary sinus and the exterior surface of the distal balloon.

14. A method for securing a medical device in a desired position within a patient and delivering fluid to the patient when performing a surgical procedure on the patient, the device including a shaft extending from a proximal end to a distal end, a distal balloon having an exterior surface connected to the shaft adjacent the distal end of the shaft, and an elongate projection extending outward from the exterior surface of the distal balloon, the projection having a base connected to the exterior surface of the distal balloon and a tip opposite the base, the method comprising;

guiding the distal end of said shaft to the desired position within the patient;

inflating the distal balloon to engage the tip of the elongate projection with tissue of the patient but maintaining the exterior surface of the distal balloon spaced from and not in contact with the tissue to secure the shaft in said desired position while providing a space between the exterior surface of the distal balloon and the tissue so that fluid can flow longitudinally along the shaft between the exterior surface of the distal balloon and the tissue; and delivering fluid from within the shaft to the patient through a lateral hole in the shaft positioned between the distal balloon and said proximal end such that at least some of said fluid flows longitudinally along the shaft between the exterior surface of the distal balloon and the tissue.

15. A medical device for delivering fluid from a fluid source to a coronary passageway in a patient during a surgical procedure on the patient, the device comprising:

an elongate tubular shaft having an outer surface extending from a proximal end to a distal end, an inner passage in fluid communication with the fluid source during use of the device, and a lateral hole in the outer surface in fluid communication with the inner passage for delivering fluid from the device in a generally lateral direction relative to the shaft during surgery;

a distal balloon connected to the shaft having an exterior surface and an interior surface opposite the exterior surface, the distal balloon being configured to engage tissue of the patient to retain the shaft in a desired position within the patient by preventing the shaft from moving in a proximal direction when the distal balloon is inflated during surgery;

a proximal balloon connected to the shaft between the distal balloon and the proximal end of the shaft, the proximal balloon having proximal and distal ends, the proximal balloon having a diameter and an exterior surface sized when expanded to engage tissue of the patient, the proximal balloon being configured to bias the shaft in the proximal direction away from the distal balloon thereby tensioning the shaft between the distal balloon and the proximal balloon;

a disk on the proximal end of the proximal balloon, the disk having a diameter greater than the diameter of the proximal balloon when expanded, the disk defining an annular distally facing edge margin extending radially beyond the exterior surface of the proximal balloon at the proximal end of the proximal balloon, the edge margin being sized for engaging coronary tissue defining an orifice leading to the coronary passageway; and wherein said lateral hole is positioned in the outer surface of the shaft between said distal balloon and said proximal balloon.

16. A medical device as set forth in claim 15 wherein the proximal balloon has a conical shape tapering from the proximal end to the distal end of the proximal balloon.

17. A medical device as set forth in claim 15 wherein the distal balloon has at least one projection extending outward from the exterior surface of the distal balloon, the projection having a base connected to the exterior surface of the distal balloon and a tip opposite the base, the tip being positioned to engage tissue of the patient to retain the shaft in a desired position within the patient by preventing the shaft from moving in a proximal direction when the balloon is inflated during surgery and the exterior surface of the distal balloon is spaced from and not in contact with the tissue; and wherein when the proximal balloon and the distal balloon are inflated during surgery the proximal balloon blocks flow of fluid longitudinally along the shaft between the proximal balloon and the tissue and the distal balloon allows flow of fluid longitudinally along the shaft between the exterior surface of the distal balloon and the tissue.

* * * * *